United States Patent [19]

Ochiai et al.

[11] 4,145,540
[45] Mar. 20, 1979

[54] 7β-PHOSPHORAMIDO-7α-METHOXYCEPHALOSPORANIC ACID DERIVATIVES

[75] Inventors: Michihiko Ochiai, Suita; Akira Morimoto, Ikeda; Osami Aki, Kawanishi; Taiiti Okada, Kyoto, all of Japan

[73] Assignee: Takeda Chemical Industries, Ltd., Osaka, Japan

[21] Appl. No.: 708,755

[22] Filed: Jul. 26, 1976

[30] Foreign Application Priority Data

Jul. 24, 1975 [JP] Japan .................. 50-90743

[51] Int. Cl.² .......................... C07D 501/18
[52] U.S. Cl. .................... 544/21; 424/246; 260/239.1
[58] Field of Search ............ 260/243 C; 544/21

[56] References Cited

U.S. PATENT DOCUMENTS

| | | | |
|---|---|---|---|
| 3,978,053 | 8/1976 | Hanma et al. | 260/243 C |
| 3,980,644 | 9/1976 | Lunn | 544/21 |
| 3,987,040 | 10/1976 | Cheng et al. | 544/21 |
| 3,997,528 | 12/1976 | Yoshioka et al. | 260/243 C |
| 3,998,817 | 12/1976 | Fukumura et al. | 260/243 C |
| 4,043,991 | 8/1977 | Hamma et al. | 544/26 |

FOREIGN PATENT DOCUMENTS

| | | |
|---|---|---|
| 2512670 | 9/1975 | Fed. Rep. of Germany. |
| 2121746 | 8/1972 | France. |
| 2170051 | 1/1973 | France. |

OTHER PUBLICATIONS

Tetrahedron Letters No. 16, pp. 1307–1310 (1976).
Tetrahedron Letters No. 14, pp. 1307–1310 (1974).

Primary Examiner—Nicholas S. Rizzo
Attorney, Agent, or Firm—Wenderoth, Lind & Ponack

[57] ABSTRACT

Cephem and penam compounds having a partial structure of formula (II):

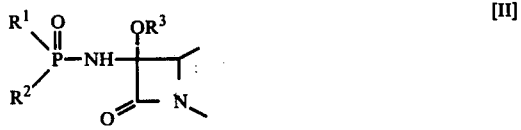

wherein $R^1$ and $R^2$, respectively, represent a hydrocarbon group which is attached to P, either directly or through an oxygen atom, and which may optionally be substituted, and $R^3$ is a hydrocarbon residue, are useful as intermediates for synthetic penicillins and cephalosporins, which in turn are useful as antibiotics or intermediates for some other synthetic penicillins and cephalosporins having antibiotic activity. To the 6- or 7-amino group of these penam or cephem compounds an objective acyl group can be introduced to give 6- or 7-acyl amino compound in a good yield, without isomerization of 6α-or 7α-substituent $OR^3$ of the penam or cephem compounds.

12 Claims, No Drawings

7β-PHOSPHORAMIDO-7α-METHOXYCEPH-ALOSPORANIC ACID DERIVATIVES

The present invention relates to novel cephem and penam compounds having a partial structure represented by the formula (II):

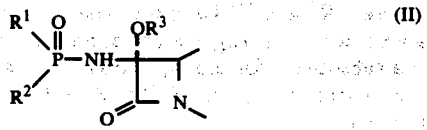

wherein $R^1$ and $R^2$, respectively, mean a hydrocarbon group which is attached to P, either directly or through an oxygen atom, and which may optionally be substituted, and $R^3$ is a hydrocarbon group, which are useful as intermediates for the synthesis of a variety of synthetic penicillins and cephalosporins having antibiotic activity, and to a process for the production thereof.

The present invention also relates to a novel and industrially feasible process for producing a cephem or penam compound having a partial structure of the formula (I):

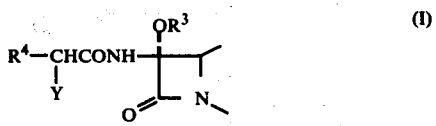

wherein $R^4$ is an organic residue, Y is hydrogen or an amino, hydroxyl, carboxyl or sulfo group which may optionally be protected, and $R^3$ has the same meaning as defined above, i.e. a cephalosporin or penicillin compound having a hydrocarbon-oxy group in the 7- or 6-position, which are useful not only as antibiotics but also as intermediates for the synthesis of a variety of synthetic penicillins and cephalosporins.

The above compound (II) can be protected by reacting a cephem or penam compound having a partial structure of the formula (V)

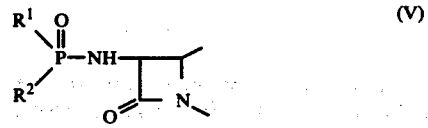

wherein $R^1$ and $R^2$ have the same meaning as defined above, with a halogenating agent and a compound of the formula (VI):

R³OH    (VI)

wherein $R^3$ has the same meaning as defined above, in the presence of a base. The resultant cephem or penam compound (II) may be reacted with a compound of the formula (III):

wherein $R^4$ and Y have the same meaning as defined above, or a reactive derivative thereof in the presence of a base, followed by treating the resultant compound with water to produce compound (I).

It is known that there is a class of cephalosporin antibiotic compounds each having a methoxy group on the carbon atom in the 7-position of the cephalosporin molecule. For example, 7α-methoxycephalosporin C and 7β-(5-amino-5-carboxyvaleramido)-7α-methoxy-3-carbamoylxymethyl-3-cephem-4-carboxylic acid are produced by fermentative culture of *Streptomyces lipmanii* and *Streptomyces clavulgerus* [R, Nagarajan et al., J. Am. Chem. Soc., 93, 2308(1971)]. Moreover, many 7β-acyl-7α-methoxycephalosporin antibiotics have been produced by introducing a methoxy group directly to the carbon atom in the 7-position of the respective cephalosporin molecules [Japanese Patent Application Laid Opens No. 62791/1973 and No. 85595/1973].

In the latter process, a 7-acylaminocephalosporin compound is reacted with a halogenating agent in the presence of a base and, then, with methanol to obtain a 7β-acylamino-7α-methoxycephalosporin compound. It is, however, not always possible, by this method, to introduce methoxy to all 7-acylaminocephalosporin compounds. For instance, the process cannot be successfully applied to 7-acylaminocephalosporins having some acyl moieties susceptible to halogenation. It is known that there is also a method which comprises removing the acyl moiety from a 7β-acyl-7α-methoxycephalosporin by way of treatment with PCl₅/pyridine/methanol, a procedure which has also been employed for deacylation of cephalosporin C, to obtain 7β-amino-7α-methoxycephalosporanic acid, but this compound is known to be so unstable that it readily isomerizes to 7β-methoxy-7α-aminocephalosporanic acid [W. H. W. Lun et al., Tetrahedron Letters, 1307 (1974)].

Under these circumstances, the present inventors have made extensive studies to find a novel and advantageous route for the production of the cephalosporin and penicillin compounds (I). As the results of the studies, the present inventors have quite unexpectedly found that a compound (II) can be produced in a good yield by reacting a compound (V) with halogenating agent and a compound (VI) in the presence of a base, and that direct conversion of a substituted phosphor group of the compound (II) (e.g. dimethylphosphor) into an acyl group (e.g. phenylacetyl) occurs without isomerization of 6α-or 7α-substituent of the compound (II) (e.g. α-methoxy) by reacting this compound (II) with a compound (III) in the presence of a base and treating the resultant compound with water.

The present invention has been accomplished on the basis of these findings.

Referring to the first starting compound (V) according to the present invention, $R^1$ and $R^2$, respectively, mean a hydrocarbon group which is attached to P, either directly or through an oxygen atom, and which may optionally be substituted. The said hydrocarbon group is exemplified by alkyl groups having 1 to 8 carbon atoms such as methyl, ethyl, propyl, isopropyl, butyl, t-butyl, pentyl, hexyl, heptyl, octyl, etc., aralkyl groups such as benzyl, phenethyl, etc., and aryl groups such as phenyl and naphthyl. These hydrocarbon groups may be substituted by lower alkyl groups having 1 to 3 carbon atoms such as methyl, ethyl, propyl, isopropyl, etc.; nitro; lower alkoxy groups having 1 to 4 carbon atoms such as methoxy, ethoxy, propoxy, t-butoxy, etc.; and halogens such as chlorine, bromine, etc.

Among the hydrocarbon groups, a lower alkyl group having 1 to 4 carbon atoms or a lower alkyl group having 1 to 4 carbon atoms substituted by halogen such as methyl, ethyl, propyl, β,β,β-trichloroethyl, butyl, isopropyl, β,β,β-tribromoethyl, benzyl, phenyl and phenyl substituted by one member selected from the group consisting of nitro, methyl, methoxy and halogen (e.g. chlorine) such as p-nitrophenyl, p-methylphenyl, p-methoxyphenyl, m-chlorophenyl are preferred as $R^1$ and $R^2$. When the hydrocarbon group is attached to P through an oxygen atom, such hydrocarbon group attached to P means a hydrocarbon-oxy group represented by the formulae

wherein $R^1$ and $R^2$ have the same meaning as defined above.

As the hydrocarbon-oxy group, lower alkoxy group having 1 to 4 carbon atoms or a lower alkoxy group having 1 to 4 carbon atoms substituted by halogen such as methoxy, ethoxy, propoxy, β,β,β-trichloroethoxy, butoxy, isopropoxy, β,β,β-tribromoethoxy, benzyloxy, phenyloxy and phenyloxy substituted by one member selected from the group consisting of nitro, methyl, methoxy, halogen (e.g. chlorine) such as p-nitrophenyloxy, p-methylphenyloxy, p-methoxyphenyloxy, m-chlorophenyloxy are preferred.

The hydrocarbon group represented by $R^3$ is exemplified by lower alkyl having 1 to 3 carbon atoms such as methyl, ethyl, propyl, and among them methyl group is preferred.

Where the starting compound (V) is a penam compound, it means a 2,2-dimethylpenam-3-carboxylic acid having a group

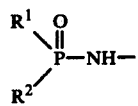

in 6-position represented by the formula (V)-a:

(V)-a wherein $R^1$ and $R^2$ have the same meaning as defined above, and R is a hydrogen atom or an ester residue, or a salt thereof.

Where the starting material (V) is a cephem compound, it means a 3-substituted 2-or 3-cephem-4-carboxylic acid having a group

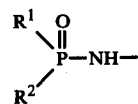

in 7-position represented by the formula (V)-b:

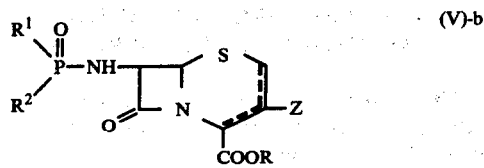

(V)-b wherein $R^1$ and $R^2$ have the same meaning as defined above, R is a hydrogen atom or an ester residue, and Z is a substituent for the 3-position, or a salt thereof. As the cephem compound (V)-b, 3-cephem compound is preferred.

It is of course to be understood that, in all the compounds herein shown by the partial structural formulae which are employed in the present invention, the moieties not shown by such partial formulae should be construed as being covered by the above description of the above compound (V), therefore, the compounds of the partial structure of the formulae (I) and (II) mean the compounds of the following formulae (I)-a, (I)-b, (II)-a and (II)-b respectively;

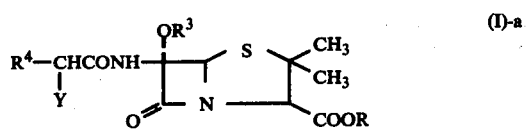

(I)-a

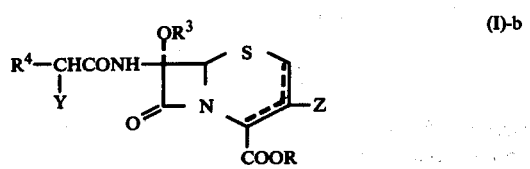

(I)-b

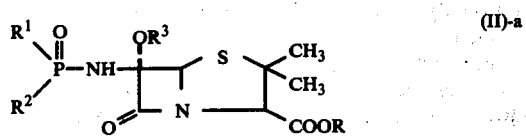

(II)-a

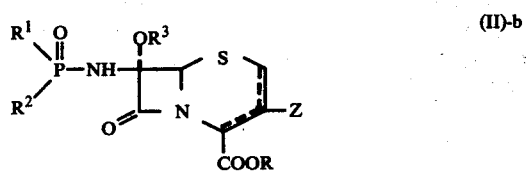

(II)-b wherein, all the symbols have the same meaning as defined above. As the cephem compounds (I)-b and (II)-b, 3-cephem compounds are preferred, respectively.

The substituent Z in 3-position of the cephem compound may be any 3-substituent of known cephalosporin compounds. Generally use is made of such a group derived from a cephalosporin compound easily obtained from a fermentation process or a group which can be easily derived from the first-mentioned group, e.g. a group having the formula: —CH$_2$X. X is exemplified by hydrogen, hydroxyl, lower alkoxy having 1 to 3 carbon atoms (e.g. methoxy, ethoxy, propoxy, etc.), mercapto, lower alkylthio having 1 to 3 carbon atoms (e.g. methylthio, ethylthio, propylthio, etc.), cyano, azido, amino, carbamoyloxy, carbamoylthio, thiocarbamoylthio or the like; or, those groups as substituted by lower alkyl having 1 to 3 carbon atoms (e.g. methyl, ethyl, propyl, etc.), lower aliphatic acyloxy having 2 to 4 carbon atoms (e.g. acetyloxy, propionyloxy, butyryloxy), aromatic acyloxy (e.g. benzoyloxy, p-chlorobenzoyloxy, etc.), quaternary ammonium groups, hydroxyphenyl, sulfamoyloxy, lower alkylsulfonyloxy having 1 to 3 carbon atoms (e.g. methylsulfonyloxy), (cis-1,2-epoxypropyl)phosphono and so forth. X may also mean a heterocyclic ring attached through a sulfur atom. The heterocyclic ring herein means a five- to six-membered ring containing 1 to 4 hetero-atoms selected from the group consisting of O, S and N, the common species of such ring including pyridyl, N-oxide-pyridyl, pyrimidyl, pyridazinyl, N-oxide-pyridazinyl, pyrazolyl, diazolyl, thiazolyl, 1,2,3-thiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl and so forth.

On these heterocyclic rings, there may occur such substituents as lower alkyl groups having 1 to 3 carbon atoms (e.g. methyl, ethyl, propyl, etc.); lower alkoxy groups having 1 to 3 carbon atoms (e.g. methoxy, ethoxy, propoxy, etc.); halogens (e.g. chlorine, bromine, etc.); trihalogenoalkyl groups (e.g. trifluoromethyl, trichloroethyl, etc.); hydroxyl; mercapto; amino; carboxyl; carbamoyl; and so forth. The quaternary ammonium group is ordinarily exemplified by pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium, lutidinium and so forth.

In a case wherein the substituent Z is susceptible to the reaction for the production of the compound (II) or compound (I), Z is protected by a conventional protecting group mentioned hereinafter according to a per se conventional method. Thus, in the reaction for the production of the compound (II) or (I), the compound (V) or compound (II) is used after converting Z thereof to a group unsusceptible to the reaction or a group which does not take part in the reaction.

The sulfur atom of the cephem or penam ring may be in the oxide-form. As examples of the ester residue represented by R, as the case may be, there may be mentioned easily removable ester residue such as benzyl, p-nitrobenzyl, p-halogenobenyl (e.g. p-bromobenzyl), alkanoyloxymethyl (e.g. pivaloyloxymethyl), di- or tri-alkylsilyl (e.g. dimethylsilyl, trimethylsilyl), alkoxysilyl (e.g. methoxysilyl, benzhydryl, alkoxyalkyl (e.g. methoxymethyl), trichloroethyl, methylsulfonylethyl, benzoylmethyl, t-butyl, methoxybenzyl, trityl, methylthiomethyl; biologically active ester residue such as acyloxymethyl (e.g. pivaloyloxymethyl), α-acetoxybutyl and α-acyloxy-α-substituted methyl (e.g. 1-pivaloyloxyethane-1-yl).

As the ester residue, easily removable ester residue such as benzyl, p-nitrobenzyl, p-bromobenzyl, benzhydryl, methylsulfonylethyl, methoxymethyl, trimethylsilyl and t-butyl are preferred from a practical point of view.

As the salt of the compounds (I), (II) and (V), there may be, for example, sodium, potassium, lithium, triethylammonium, and tributylammonium salt.

In the reactions of the present invention described hereinbefore, the compound (II) or (V) may be used advantageously in an ester-form thereof.

The compound (II) can be produced by reacting a compound (V) or a salt thereof with a halogenating agent and a compound (VI) in the presence of a base. As the base to be employed in this reaction, there may be mentioned metal salt of alcohol of the formula (VIII):

$$MOR^3 \quad (VIII)$$

wherein M is an alkali metal or alkaline earth metal such as lithium, sodium, potassium and magnesium, and $R^3$ has the same meaning as previously defined, such as lithium methoxide, lithium ethoxide, lithium benzyloxide, sodium phenoxide, sodium methoxide; lower alkyl lithium such as methyl lithium, n-butyllithium, phenyllithium; alkali metal hydride such as sodium hydride, potassium hydride; potassium t-butoxide and so forth.

This reaction is desirably conducted in an inert solvent, e.g. tetrahydrofuran, dimethoxyethane or dimethylformamide, for example at a temperature between $-80°$ C. and $0°$ C. Thus, compound (V) is reacted with compound (VI) and a halogenating agent, the proportion of which should be at least one molecular equivalent. Said halogenating agent is exemplified by halogen such as chlorine, bromine; N-halogenoamides and N-halogenoimides such as N-chlorosuccinimide, N-bromosuccinimide, N-chloroacetamide, etc., N-halogenosulfonamides, e.g. N-chlorobenzenesulfonamide, N-chloro-p-toluenesulfonamide, etc.; N-halogenobenzotriazoles, e.g. 1-bromobenzotriazole, etc.; organic hypochlorites, e.g. t-butyl hypochlorite, t-butyl hypobromite; and so forth.

Among thus obtained compounds of the formula (II), i.e. the formulae (II)-a and (II)-b, there may be the following compounds;

1. p-Nitrobenzyl 7α-Methoxy-7β-dimethylphosphoramido-3-carbamoyloxymethyl-3-cephem-4-carboxylate
2. t-Butyl 7α-methoxy-7β-diethylphosphoramido-3-azidomethyl-3-cephem-4-carboxylate
3. Benzhydryl 7α-methoxy-7β-dibenzylphosphoramido-3-methoxymethyl-3-cephem-4-carboxylate
4. Benzhydryl 7α-methoxy-7β-(di-p-nitrophenylphosphoramido)-3-(5-methyl-1,3,4-thiadiazol-2-yl)thiomethyl-3-cephem-4-carboxylate
5. Benzhydryl 7α-methoxy-7β-dimethylphosphoramido-3-(1-methyl-1H-tetrazol-5-yl)thiomethyl-3-cephem-4-carboxylate
6. p-Bromobenzyl 7α-methoxy-7β-(di-p-methylphenylphosphoramido)-3-carbamoyloxymethyl-3-cephem-4-carboxylate
7. t-Butyl 7α-methoxy-7β-(di-n-butylphosphoramido)-3-(5-methyl-1,3,4-oxadiazol-2-yl)thiomethyl-3-cephem-4-carboxylate
8. Methoxymethyl 6α-methoxy-6β-diphenylphosphoramidopenicillanate
9. Benzhydryl 7α-methoxy-7β-(di-n-propylphosphoramido)-3-methylthiomethyl-3-cephem-4-carboxylate
10. t-Butyl 7α-methoxy-7β-(di-p-methoxyphenylphosphoramido)-3-(1-methyl-1H-tetrazol-5-yl)thiomethyl-3-cephem-4-carboxylate
11. t-Butyl 7α-methoxy-7β-(di-p-methylphenylphosphoramido)-3-carbamoyloxymethyl-3-cephem-4-carboxylate
12. t-Butyl 7α-methoxy-7β-dimethylphosphoramido-3-thiocarbamoylthiomethyl-3-cephem-4-carboxylate 13. Methanesulfonylethyl 6α-methoxy-6β-dimethylphosphoramidopenicillanate
14. Benzhydryl 7α-methoxy-7β-dimethylphosphoramido-3-(N-methylcarbamoyloxymethyl)-3-cephem-4-carboxylate
15. Methoxymethyl 7α-methoxy-7β-dimethylphosphoramido-3-(1-methyl-1H-tetrazol-5-yl)thiomethyl-3-cephem-4-carboxylate
16. Methylsulfonylethyl 7α-methoxy-7β-dimethylphosphoramido-3-(1-methyl-1H-tetrazol-5-yl)thiomethyl-3-cephem-4-carboxylate
17. t-Butyl 7α-methoxy-7β-dimethylphosphoramido-3-(5-methyl-1,3,4-thiadiazol-2-yl)thiomethyl-3-cephem-4-carboxylate
18. t-Butyl 7α-methoxy-7β-dimethylphosphoroamido-3-(1H-1,2,3-triazol-5-yl)thiomethyl-3-cephem-4-carboxylate
19. t-Butyl 7α-methoxy-7β-(di-m-chlorophenylphosphoramido)-3-carbamoyloxymethyl-3-cephem-4-carboxylate The compound (I) can be produced by reacting thus produced compound (II) with a compound (III) or a reactive derivative at the carboxyl group thereof in the presence of a base, and treating the resultant compound with water.

As examples of the base to be employed in this reaction, there may be mentioned alkyl lithium-tertiary amine complexes, e.g. n-butyl lithium-triethylamine; n-butylamine-1,4-diazabicyclo-[2,2,2]octane; the same lower alkyl lithium and alkali metal hydride as used in the reaction between compound (V) and compound (VI), and so forth.

In this reaction, a carboxylic acid of the formula (II) may be employed as a free acid, a salt thereof or as a reactive derivative thereof. As the salt there may be exemplified alkali or alkali earth metal salt such as sodium, potassium, calcium-salt, or organic tertiary amine salt such as trimethylamine, pyridine-salt. As the reactive derivative of the compound (III), there may be exemplified acid halide (e.g. chloride, bromide); acid anhydride; mixed acid anhydride; active amide; active ester; or the like. As examples of said active ester, there may be mentioned p-nitrophenyl ester, 2,4-dinitrophenyl ester, pentachlorophenyl ester, N-hydroxysuccinimide ester, N-hydroxyphthalimide ester and so forth. As examples of said mixed acid anhydride, there may be mentioned mixed acid anhydrides with carbonic acid monoesters such as carbonic acid monomethyl ester, carbonic acid monoisobutyl ester, etc., and mixed acid anhydrides with lower alkanoic acids which may optionally be substituted by halogen and the like, e.g. pivalic acid, trichloroacetic acid and so forth. Where the carboxylic acid is used as the free acid or as a salt thereof, use is made of a suitable condensing agent, which is exemplified by N,N'-disubstituted carbodiimides, e.g. N,N'-dicyclohexylcarbodiimide, etc.; azolides, e.g. N,N'-carbonyldiimidazole, N,N'-thionyldiimidazole, etc.; and such dehydrating agents as N-ethoxycarbonyl-2-ethoxy-1,2-dihydroquinoline, phosphorus oxychloride, alkoxyacetylenes and so forth. It is likely that when such a condensing agent is employed, the reaction proceeds through the formation of a reactive derivative of the carboxylic acid.

As examples of the acyl group of carboxylic acid (III), i.e. the acyl group represented by the formula (A)

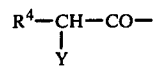

wherein $R^4$ and Y have the same meaning as defined above, there may be mentioned aliphatic carboxylic acid acyl groups such as acetyl, propionyl, hexanoyl, butanoyl, heptanoyl, octanoyl, cyclopentanoyl, etc.; mono-substituted aliphatic carboxylic acid acyl groups such as phenylacetyl, phenoxyacetyl, 2-thienylacetyl, tetrazolylthioacetyl, tetrazolylacetyl, cyanoacetyl, phenoxyacetyl, acetoacetyl, ω-halogenoacetoacetyl, 4-methylthio-3-oxobutyryl, 4-carbamoylmethylthio-3-oxobutyryl, α-phenoxypropionyl, α-phenoxybutyroyl, p-nitrophenylacetyl, α-(2-pyridyloxy)acetyl, α-(3-pyridyloxy)acetyl, α-(4-pyridyloxy)acetyl, 2-(2-hydroxythiazol-4-yl)acetyl, 2-(2-aminothiazol-4-yl)acetyl, 4-pyridylthioacetyl, 2-(3-sydnone)acetyl, 1-pyrazolylacetyl, 2-furylacetyl, 6-(2'-oxo-3'-methylpyridazinyl)thioacetyl, etc.; di-substituted aliphatic carboxylic acid acyl groups such as α-carboxyphenylacetyl, α-aminophenylacetyl, mandelyl, α-sulfophenylacetyl, α-sulfo-(p-aminophenyl)acetyl, phenylglycyl, 1-cyclohexenylglycyl, thienylglycyl, furylglycyl, cyclohexanedienylglycyl, α-(β-methylsulfonylethoxycarbonyl)-aminophenylacetyl, 5-amino-5-carboxybutyryl, etc.; aromatic acyl groups such as benzoyl, p-nitrobenzoyl, etc.; and heterocyclic acyl groups such as 5-methyl-3-phenyl-4-isoxazolylcarbonyl, 3-(2,6-dichlorophenyl)-5-methyl-4-isoxazolylcarbonyl,,etc.

The amino, hydroxyl, sulfo and carboxyl group represented by Y of the acyl group (A), as well as these functional groups included in the organic residue $R^4$ and the substituent Z, may be desirably protected. As protecting groups for amino group, use may be made of any conventional protecting group for an amino group. As such protecting group, there may be mentioned aromatic acyl groups such as phthaloyl, benzoyl, p-nitrobenzoyl, toluoyl, naphthoyl, p-tert-butylbenzoyl, p-tert-butylbenzenesulfonyl, phenylacetyl, benzenesulfonyl, phenoxyacetyl, toluenesulfonyl, chlorobenzoyl, etc.; aliphatic acyl groups such as acetyl, valeryl, capryryl, n-decanoyl, acryloyl, pivaloyl, camphorsulfonyl, methanesulfonyl, chloroacetyl, etc.; esterified carboxyl groups such as ethoxycarbonyl, isobornyloxycarbonyl, phenyloxycarbonyl, trichloroethoxycarbonyl, benzyloxycarbonyl, etc.; carbamoyl groups such as methylcarbamoyl, phenylcarbamoyl, naphthylcarbamoyl, etc. and the corresponding thiocarbamoyl groups; and so forth. As protecting groups for carboxyl group, use may be made of any conventional protecting group for carboxyl group. As such protecting group, there may be mentioned lower alkyl such as methyl, ethyl, tert-butyl, tert-amyl; aralkyl or substituted aralkyl such as benzyl, p-nitrobenzyl, p-methoxybenzyl, benzhydryl; 1-indanyl; phenacyl; aryl or substituted aryl such as phenyl, p-nitrophenyl; lower alkoxy substituted lower alkyl such as methoxymethyl, ethoxymethyl, acyloxy substituted lower alkyl such as benzyloxymethyl, acetoxymethyl, pivaloyloxymethyl; β-methylsulfonylethyl; methylthiomethyl; trityl; β,β,β-trichloroethyl; silyl groups such as trimethylsilyl, dimethylsilyl, etc. As protecting groups for hydroxyl and sulfo groups, use may be made of any conventional protecting groups for hydroxyl and sulfo groups respectively. As such protecting group for hydroxyl group, there may be mentioned acyl groups such as formyl, dichloroacetyl, trichloroacetyl, etc.; tetrahydropyranyl, β,β,β-trichloroethoxycarbonyl, benzyl and so forth. As such protective groups for sulfo group, there may be mentioned methyl, ethyl, isopropyl, t-butyl, benzyl, β,β,β-trichloroethyl and so forth.

The organic residue represented by $R^4$ means an organic residue derived from the acyl group (A) by eliminating

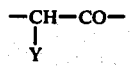

thereof. Particularly desirable species of $R^4$ are phenyl, five- or six-membered heterocyclic rings containing from 1 to 4 hetero-atoms selected from the group consisting of sulfur, oxygen and nitrogen atoms and these phenyl and five- or six-membered heterocyclic rings which are attached to the

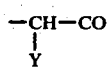

group through as oxygen or sulfur atom.

As such five or six-membered heterocyclic ring, there may be mentioned thiazol or 2-substituted thiazol such as 2-hydroxythiazol-4-yl, 2-aminothiazol-4-yl; pyrazolyl such as 1-pyrazolyl; furyl such as 2-furyl, pyridyloxy or pyridylthio such as 2-, 3- or 4-pyridyloxy, 4-pyridylthio.

The process for producing the compound (I) is conducted first by reacting the compound (II) with a compound (III) or reactive derivative thereof in the presence of a base. This reaction is generally carried out in a solvent which is inert to this reaction. The solvent may for example by any of such common solvents as tetrahydrofuran, dimethoxyethane, dimethylformamide, hexamethylphosphoramide and so forth. The reaction is generally conducted at a temperature between 0° C. and −80° C.

In the first step of the process, t-butyl 7β-phenylketeneimino-7α-methoxydesacetoxycephalosporanate and benzhydryl 7β-phenylketeneimino-7α-methoxycephalosporanate can be isolated. This fact might show that the compound having a partial structure of the formula (IV):

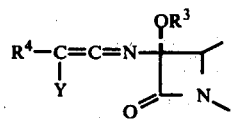

wherein $R^3$, $R^4$ and Y have the same meaning as defined above, could be formed intermediately in the process. The resultant reaction product in the first step is then treated with water to give the compound (I). This treatment with water is preferably in the presence of acid. As said acid, hydrochloric acid, sulfuric acid, acetic acid, formic acid, oxalic acid, p-toluenesulfonic acid, etc. may be employed with advantage.

The resultant reaction product is a highly reactive compound. The compound (I) may also be obtained by allowing the isolated keteneimino compound (IV) to stand, or by treating the compound (IV) by chromatography on silica gel or with acid, for instance.

In the method of the present invention, either before or after each step described hereinbefore each of the compounds may be subjected to suitable treatments such as desalting, salt inter-conversion, esterification, de-esterification, oxidation, de-oxidation, a conversion reaction at 3-position of the cephem compound, protection of any functional group, removal of protective groups, if any, and so forth.

The starting compound of formula (V) may for example be produced by reacting a cephem or penam compound having a partial structure of formula (VII):

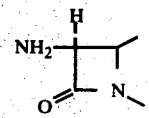

with a compound of the formula (VIII):

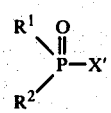

wherein $R^1$ and $R^2$ are as previously defined; X' is halogen (e.g. chlorine, bromine).

As the compound (VIII), there may for example be dimethylphosphinyl chloride, diethylphosphinyl chloride, diphenylphosphinyl chloride, di-(β,β,β-trichloroethyl)phosphinyl chloride, dibenzylphosphinyl chloride, dimethyl phosphorochloridate, diethylphosphorochloridate, diphenyl phosphorochloridate, dibenzylphosphorochloridate, di(β,β,β-trichloroethyl)phosphorochloridate, di-(β-cyanoethyl)phosphorochloridate, di-(p-nitrophenyl)phosphorochloridate and the like.

The above reaction is preferably carried out in the presence of a base, such as a tertiary amine, e.g. triethylamine, pyridine, diethylaniline, etc., or an inorganic base, e.g. sodium hydrogen carbonate, potassium dihydrogen phosphate, sodium hydroxide, etc. This reaction may be carried out in a solvent that will not interfere with it, such as water, acetone, ethyl acetate, acetonitrile, dimethylformamide or dimethylacetamide.

The compound (III) may be produced for example according a method described in German Patent Application P25 34 850.9, or according to a similar method thereto, and the reactive derivatives of the compound (III) may be produced by a conventional method from a free carboxylic acid (III).

The compound (I) thus obtained, if necessary, is further treated for removal of protective groups in the conventional manner. For example, where the 3- or 4-position of compound (I) is an ester, the free acid compound may be obtained by removing the ester, e.g. by hydrolysis or hydrogenolysis which is conventional per se. Taking the benzyl, diphenylmethyl, p-nitrobenzyl and 3,5-dimethoxybenzyl esters as examples, these esters may be removed by hydrogenolysis, e.g. by reacting the esters with hydrogen in an inert solvent and in the presence of a 10% palladium-on-carbon catalyst. A 2,2,2-trichloroethyl group may be removed by reacting the ester with zinc and formic acid or glacial acetic acid. A t-butyl group may be removed by means of trifluoroacetic acid-anisole. Other known protective groups for carboxyl group may be removed by procedures known per se. If necessary, the free acid product may be converted to the salt of sodium or potassium. Where the amino group has been protected by an acyl group, the free amino compound (I) may be obtained by a deacylation procedure known per se to be suited for the particular acyl group, for example by treatment with an acid (e.g. trifluoroacetic acid, hydrogen chloride) in the case of formyl, amyloxycarbonyl and t-butoxycarbonyl; by reduction in the case of 2,2,2-trichloroethoxycarbonyl, benzyloxycarbonyl and p-nitrobenzyloxycarbonyl; or by treatment with alkali (e.g. sodium hydroxide, potassium hydroxide) in the case of 2-methylsulfonylethoxycarbonyl. Where the sulfur atom on the cephem or penam ring of compound (I) is in the oxideform, it may be de-oxidized in a manner conventional per se. The 2-cephem compound may be converted to the 3-cephem compound in a manner conventional per se.

If the compound (I) is a cephalosporin compound having an acetoxymethyl, acetoacetoxymethyl or carbamoyloxymethyl group in 3-position, it may be reacted with a thiol or tertiary amine, for example, with such a thiol or tertiary amine as that corresponding to X mentioned hereinbefore, by a method conventional per se to obtain the corresponding 3-substituted compound.

The compounds (I) obtainable by the foregoing method are of value as antibiotics which are active both against Gram-positive bacteria and against Gram-negative bacteria and which, at the same time, are resistant to β-lactamases, or as intermediates for such antibiotics as mentioned above, for example, 7α-methoxy-7β-(2-aminothiazol-4-ylacetamido)-3-(1-methyl-1H-tetrazol-5-ylthiomethyl)-3-cephem-4-carboxylic acid, i.e. a known cephalosporin compound.

Namely, the compounds (I) have antibiotic activity against Gram-negative and Gram-positive bacteria such as *Escherichia coli*, *Serratia marcescens*, *Proteus vulgaris*, *Pseudomonas aeruginosa* and so on. Therefore, these compounds are of use in the treatment of infections with the aforementioned bacteria in man and animals, giving therapeutic effects. Like the known cephalosporin or penicillin drugs, the compounds (I) may each be administered to patients in such dosage forms as injections, capsules, tablets, granules, etc. and, if necessary, together with a physiologically acceptable vehicle or excipient, as solutions, suspensions, solid preparations and so on.

Specifically, sodium 7α-methoxy-7β-(2-aminothiazol-4-ylacetamido)-3-(1-methyl-1H-tetrazol-5-ylthiomethyl)-3-cephem-4-carboxylate, for instance, or any other of compounds (I) is administered intramuscularly at a daily dose level of about 5 to 20 milligrams per kilogram body weight in three to five divided doses daily and this therapy is particularly effective in the treatment of respiratory and urinary tract infections.

Compounds (II) of the present invention are useful as intermediates for the synthetic penicillins and cephalosporins having antibiotic activity, for example, compounds (I) including such known compound as mentioned just above, and by using the compound (II) as a starting compound the compound (I) can be produced in a good yield without isomerization of 6α- or 7α-substituent of the compound (II).

REFERENCE EXAMPLE 1 t-Butyl 7β-dimethylphosphoramidodesacetoxycephalosporanate

In dichloromethane (40 ml) is dissolved t-butyl 7β-aminodesacetoxycephalosporanate (8.10 g). To the solution is added pyridine (2.84 g) together with dimethyl phosphorochloridate (5.18 g). The mixture is stirred at room temperature for 2 hours. The reaction mixture is washed with 1N-hydrochloric acid, water, saturated aqueous solution of sodium bicarbonate and water, followed by drying over magnesium sulfate. The solvent is then distilled off to obtain an oily substance. This oily substance is crystallized from ether, filtered and dried. By this procedure is obtained 8.20 g of t-butyl 7β-dimethylphosphoramidodesacetoxycephalosporanate. Melting point: 77°–78° C.

Elemental analysis for $C_{14}H_{23}N_2O_6PS$: Calcd.: C, 44.44; H, 6.12; N, 7.40. Found: C, 44.33; H, 5.90; N, 7.18.

IR (KBr): 1770 cm$^{-1}$, 1705 cm$^{-1}$

NMR (CDCl$_3$, δ): 1.50(s,9H,t-C$_4$H$_9$), 2.09(s,3H,3-CH$_3$), 3.38 (q.2H,2-CH$_2$), 3.79(s,3H,CH$_3$O), 3.87(s,3H,CH$_3$O), 4.95(d, 1H,6-CH), 5.17(dd,1H,7-CH)

REFERENCE EXAMPLE 2

In the same manner as Reference Example 1, the following compounds are produced. The physical constants of the compounds are also shown.

t-Butyl 7β-diphenylphosphinylaminodesacetoxycephalosporanate

Melting point: 185°–188° C.

Elemental analysis for $C_{24}H_{27}N_2O_4PS$: Calcd.: C, 61.26; H, 5.78; N, 5.95. Found: C, 61.54; H, 6.04; N, 5.94.

IR(KBr): 1750 cm$^{-1}$, 1695 cm$^{-1}$

NMR(CDCl$_3$, δ): 1.53(s,9H,t-C$_4$H$_9$), 2.07(s,3H,3-CH$_3$), 3.40 (q,2H,2-CH$_2$), 4.90(d,1H,6-CH), 5.14(dd,1H,7-CH), 7.30-8.40(m,10H,C$_6$H$_5$×2)

t-Butyl 7β-diphenylphosphoramidodesacetoxycephalosporanate

Melting point: 187°–188° C.

Elemental analysis for $C_{24}H_{27}N_2O_6$: Calcd.: C, 57.36; H, 5.42; N, 5.57. Found: C, 57.13; H, 5.33; N, 5.57.

IR(KBr): 1760 cm$^{-1}$, 1750 cm$^{-1}$

NMR(CDCl$_3$, δ): 1.55(s,9H,t-C$_4$H$_9$), 2.09(s,3H,3-CH$_3$), 3.28(d, 2H,2-CH$_2$), 4.18(d,1H,NH), 4.85(d,1H,6-CH), 5.38(q, 1H,7-CH), 7.30(s,10H,C$_6$H$_5$×2)

t-Butyl 7β-di(β,β,β-trichloroethyl)phosphoramidodesacetoxycephalosporanate

Melting point: 162°–163° C.

Elemental analysis for $C_{16}H_{21}Cl_6N_2O_6PS$: Calcd.: C, 31.34; H, 3.45; N, 4.56. Found: C, 31.58; H, 3.33; N, 4.63.

IR(KBr): 1770 cm$^{-1}$, 1715 cm$^{-1}$

NMR(CDCl$_3$, δ): 1.52(s,9H,t-C$_4$H$_9$), 2.08(s,3H,3-CH$_3$), 3.38 (q,2H,2-CH$_2$), 4.60(s,2H,CCl$_3$CH$_2$), 4.72(s,2H,CCl$_3$CH$_2$), 4.88(d,1H,6-CH), 5.25(dd,1H,7-CH)

Benzhydryl 7β-di(β,β,β-trichloroethyl)phosphoramidocephalosporanate

Melting point: amorphous

IR(KBr): 1780cm$^{-1}$, 1710cm$^{-1}$

NMR(CDCl$_3$, δ): 1.98(s,3H,OCOCH$_3$), 3.41(Broad s, 2H,2-CH$_2$), 4.64(d,2H,CCl$_3$CH$_2$), 4.73(d,2H,CCl$_3$CH$_2$), 4.80–5.30 (m,4H,3-CH$_2$ and 6-CH and 7-CH), 6.92(s,1H,COOCH), 7.33(s,10H, C$_6$H$_5$×2)

Benzyl 6β-di(β,β,β-trichloroethyl)phosphoramidopenicillanate

Melting point: amorphous

IR(KBr) 1770 cm$^{-1}$, 1730 cm$^{-1}$

NMR(CDCl$_3$, δ): 1.40(s,3H,2-CH$_3$), 1.60(s,3H,2-CH$_3$), 4.47(s, 1H,3-CH), 4.60(d,2H,CCl$_3$CH$_2$), 4.71(d,2H,CCl$_3$CH$_2$), 4.95(dd,1H,6-CH), 5.17(s,2H,COOCH$_2$), 5.55(d,1H,5-CH), 7.33(s,5H,C$_6$H$_5$)

EXAMPLE 1 t-Butyl 7β-dimethylphosphoramido-7α-methoxydesacetoxycephalosporanate

In tetrahydrofuran (100 ml) is dissolved t-butyl 7β-dimethylphosphoramidodesacetoxycephalosporanate (5.00 g) and the solution is stirred under nitrogen streams and under cooling at −78° C.

A lithium methoxide-methanol solution prepared from methanol (30 ml) and lithium metal (320 mg) is cooled to −78° C. and then added in a single dose to the above solution. The reaction mixture is stirred for 5 minutes, after which time t-butyl hypochlorite (1.480 g) is added in a single dose. The reaction is conducted at −78° C. for 30 minutes and, then, to the resultant mixture acetic acid (3 ml) is added. The reaction mixture is poured in a saturated aqueous solution of sodium bicarbonate and extracted with ethyl acetate. The organic layer is taken, washed with water and dried over magnesium sulfate. The solvent is then distilled off to obtain an oily substance. This oily substance is crystallized from ether and collected by filtration. By the above procedure is obtained t-butyl 7β-dimethylphosphoramido-7α-methoxydesacetoxycephalosporanate.

Melting point: 125°–126° C.

Elemental analysis for C$_{15}$H$_{25}$N$_2$O$_7$PS: Calcd.: C, 44.11; H, 6.16; N, 6.85. Found: C, 44.52; H, 6.15; N, 6.81.

IR(KBr): 1750cm$^{-1}$, 1700cm$^{-1}$

NMR(CDCl$_3$, δ): 1.54(s,9H,t-C$_4$H$_9$), 2.14(s,3H,3-CH$_3$), 3.15 (Broad s, 2H,2-CH$_2$), 3.56(s,3H,7-OCH$_3$), 3.71(d,3H, CH$_3$O), 3.87(d,3H,CH$_3$O), 4.59(d,1H,NH), 4.86(s,1H, 6-CH)

EXAMPLE 2

In the same manner as Example 1, the compounds mentioned in Reference Example 2 are converted to the corresponding 7α-methoxy compounds. Their physical constants are also shown below.

t-Butyl 7β-diphenylphosphinylamino-7α-methoxydesacetoxycephalosporanate

Melting point: 132°–133° C.

Elemental analysis for C$_{25}$H$_{29}$N$_2$O$_5$PS: Calcd.: C, 59.98; H, 5.83; N, 5.59. Found: C, 60.47; H, 5.86; N, 5.61.

IR(KBr): 1750cm$^{-1}$, 1705cm$^{-1}$

NMR(CDCl$_3$, δ): 1.49(s,9H,t-C$_4$H$_9$), 2.10(s,3H,3-CH$_3$), 3.31 (s,2H,2-CH$_2$), 3.32(s,3H,7-OCH$_3$), 4.50(d,1H,NH), 4.88 (s,1H,6-CH), 7.30–8.40(m,10H,C$_6$H$_5$×2)

t-Butyl 7β-diphenylphosphoramido-7α-methoxydesacetoxycephalosporanate

Melting point: 120°–121° C.

Elemental Analysis for C$_{25}$H$_{29}$N$_2$O$_7$PS: Calcd.: C, 56.38; H, 5.49; N, 5.26. Found: C, 56.65; H, 5.56; N, 5.30.

IR(KBr): 1750cm$^{-1}$, 1700cm$^{-1}$

NMR(CDCl$_3$, δ): 1.50(s,9H,t-C$_4$H$_9$), 2.14(s,3H,3-CH$_3$), 3.03 (broad s, 2H,2-CH$_2$), 3.52(s,3H,7-OCH$_3$), 4.83(s,1H, 6-CH), 5.21(d,1H,NH), 7.23(s,10H,C$_6$H$_5$×2)

t-Butyl 7β-di(β,β,β-trichloroethyl)phosphoramido-7α-methoxydesacetoxycephalosporanate Melting point: 137°–138° C.

Elemental analysis for C$_{17}$H$_{23}$Cl$_6$N$_2$O$_7$PS: Calcd.: C, 31.74; H, 3.60; N, 4.35. Found: C, 31.88; H, 3.53; N, 4.44.

IR(KBr): 1750cm$^{-1}$, 1710cm$^{-1}$

NMR(CDCl$_3$, δ): 1.53(s,9H,t-C$_4$H$_9$), 2.16(s,3H,3-CH$_3$), 3.26 (s,2H,2-CH$_2$), 3.65(s,3H,7-OCH$_3$), 4.68(d,2H,CCl$_3$CH$_2$), 4.76(d,2H,CCl$_3$CH$_2$), 4.94(s,1H,7-CH), 5.00(d,1H,NH)

Benzhydryl 7β-di(β,β,β-trichloroethyl)phosphoramido-7α-methoxycephalosporanate Melting point: 104°–106° C.

Elemental analysis for C$_{28}$H$_{27}$Cl$_6$N$_2$O$_9$PS: Calcd.: C, 41.45; H, 3.35; N, 3.45. Found: C, 41.65; H, 3.41; N, 3.67.

IR(KBr): 1790cm$^{-1}$, 1730cm$^{-1}$

NMR(CDCl$_3$, δ): 2.01(s,3H,OCOCH$_3$), 3.43(s,2H,2-CH$_2$), 3.77(s, 3H,7-OCH$_3$), 4.66(d,2H,CCl$_3$CH$_2$), 4.80(d,2H,CCl$_3$CH$_2$), 4.98(s,1H,6-CH), 4.98(q,2H,3-CH$_2$), 6.98(s,1H,COOCH), 7.35(s,10H, C$_6$H$_5$×2)

Benzyl 6β-di(β,β,β-trichloroethyl)phosphoramido-6α-methoxypenicillanate

Melting point: 123°–125° C.

Elemental analysis for C$_{20}$H$_{23}$Cl$_6$N$_2$O$_7$PS: Calcd.: C, 35.37; H, 3.41; N, 4.12. Found: C, 35.58; H, 3.10; N, 4.31.

IR(KBr): 1775cm$^{-1}$,1740cm$^{-1}$

NMR(CDCl$_3$, δ): 1.36(s,3H,2-CH$_3$), 1.52(s,3H,2-CH$_3$), 3.56(s, 3H,6-OCH$_3$), 4.55(d,2H,CCl$_3$CH$_2$), 4.72(s,1H,3-CH), 4.76 (d,2H,CCl$_3$CH$_2$), 5.18(s,1H,COOCH$_2$), 5.23(d,1H,NH), 5.50(s,1H,5-CH), 7.34(s,5H,C$_6$H$_5$)

EXAMPLE 3 t-Butyl 7β-phenylketeneimino-7α-methoxydesacetoxycephalosporanate

Procedure (A)

In dimethylformamide (10 ml) is dissolved t-butyl 7β-di(β,β,β-trichloroethyl)phosphoramido-7α-methoxydesacetoxycephalosporanate (305 mg) and the solution is stirred under nitrogen streams and cooled at −20° C. To the solution is added sodium hydride (13 mg), followed by reacting for 30 minutes. To the reaction mixture is added phenylacetyl chloride (80 mg) and the reaction is further carried out for 30 minutes. The reaction mixture is poured in water and extracted with ethyl acetate. The organic layer is taken, dried over magnesium sulfate and distilled to remove the solvent. The resultant oily substance is quickly separated by chromatography on silica gel to obtain crystals of t-butyl 7β-phenylketeneimino-7α-methoxydesacetoxycephalosporanate.

Melting point: 121°–123° C.

Elemental analysis for C$_{21}$H$_{24}$N$_2$O$_4$S: Calcd.: C, 62.97; H, 6.04; N, 6.99. Found: C, 62.77; H, 5.79; N, 6.85.

IR(KBr): 2000cm$^{-1}$, 1760cm$^{-1}$, 1720cm$^{-1}$

NMR(CDCl$_3$, δ): 1.55(s,9H,t-C$_4$H$_9$), 2.14(s,3H,3-CH$_3$), 3.18(s,2H,2-CH$_2$), 3.69(s,3H,7-OCH$_3$), 4.99(s,1H,6-CH), 5.22(s,1H,CH=C—), 7.25(s,5H,C$_6$H$_5$)

Procedure (B)

In tetrahydrofuran (10 ml) is dissolved t-butyl 7β-di(β,β,β-trichloroethyl)phosphoramido-7α-methoxydesacetoxycephalosporanate (305 mg) and the solution is stirred under nitrogen streams, and cooled to −78° C. To the solution is added n-butyl lithium (0.45 ml of 9% solution in n-hexane) and the reaction is carried out for 5 minutes. Then, following the addition of phenylacetyl chloride (80 mg), the reaction is further carried out for 30 minutes. The reaction mixture is poured in water and extracted with ethyl acetate. The organic layer is washed with water and dried over magnesium sulfate. The solvent is distilled off and the resultant oily substance is quickly separated and purified by chromatography on silica gel. By the described procedure is obtained t-butyl 7β-phenylketeneimino-7α-methoxydesacetoxycephalosporanate.

Procedure (C)

In tetrahydrofuran (5 ml) is dissolved t-butyl 7β-diphenylphosphoramido-7α-methoxydesacetoxycephalosporanate (266 mg) and the solution is stirred under nitrogen streams and under cooling at −78° C. To the solution is added triethylamine (50 mg) together with n-butyl lithium (0.25 ml of 9% solution in n-hexane), and the reaction is conducted for 15 minutes. Then, to the mixture phenylacetyl chloride (77 mg) is added and the reaction is conducted at −78° C. for 30 minutes. The reaction mixture is poured in water and extracted with ethyl acetate. The organic layer is taken, washed with water and dried over magnesium sulfate. The solvent is then distilled off to obtain an oily substance. This oily substance is quickly separated and purified by chromatography on silica gel to obtain t-butyl 7β-phenylketeneimino-7α-methoxydesacetoxycephalosporanate (77 mg) and t-butyl 7β-phenylacetamido-7α-methoxydesacetoxycephalosporanate (47 mg).

EXAMPLE 4

Benzhydryl 7β-phenylacetamido-7α-methoxycephalosporanate

In tetrahydrofuran (10 ml) is dissolved benzhydryl 7β-di(β,β,β-trichloroethyl)phosphoramidocephalosporanate (811 mg) and the solution is stirred under cooling at −78° C. and under nitrogen streams. To this solution is added triethylamine (100 mg) together with n-butyl lithium (0.5 ml of 9% solution in n-hexane) and the reaction is carried out for 15 minutes. Then, following the addition of phenylacetyl chloride (154 mg), the reaction is further conducted at −78° C. for 30 minutes. The reaction mixture is poured in water and extracted with ethyl acetate. The organic layer is taken and dried over magnesium sulfate. The solvent is then distilled off to obtain an oily substance. This oily substance is promptly separated and purified by chromatography on silica gel. By the above procedure is obtained 20 mg of benzhydryl 7β-phenylketeneimino-7α-methoxycephalosporanate as a powder.

IR(KBr): 2000cm$^{-1}$, 1785cm$^{-1}$, 1740cm$^{-1}$

There also is obtained 270 mg of benzhydryl 7β-phenylacetamido-7α-methoxycephalosporanate as a powder.

EXAMPLE 5 t-Butyl 7β-phenylacetamido-7α-methoxydesacetoxycephalosporanate

Procedure (A)

In acetone (1 ml) is dissolved t-butyl 7β-phenylketeneiminodesacetoxycephalosporanate (10 mg), followed by the addition of 1N-hydrochloric acid (0.1 ml). The mixture is stirred at room temperature for 2 hours. The reaction mixture is poured in water and extracted with ethyl acetate. The organic layer is taken and washed with a saturated aqueous solution of sodium bicarbonate and water, followed by drying over magnesium sulfate. The solvent is then distilled off to obtain 8 mg of t-butyl 7β-phenylacetamido-7α-methoxydesacetoxycephalosporanate as crystals.

Procedure (B)

In tetrahydrofuran (10 ml) is dissolved t-butyl 7β-dimethylphosphoramidodesacetoxycephalosporanate (408 mg) and the solution is stirred under cooling at −78° C. and under nitrogen streams. To the solution is added triethylamine (100 mg) together with n-butyl lithium (0.5 ml of 9% solution in n-hexane), and the reaction is carried out for 15 minutes. Then, phenylacetyl chloride (154 mg) is added and the reaction is further conducted at −78° C. for 30 minutes. To the reaction mixture is added acetic acid (0.2 ml) and the reaction is carried out for 5 minutes. The reaction mixture is poured in water and extracted with ethyl acetate. The organic layer is taken, washed with a saturated aqueous solution of sodium bicarbonate and water, and dried over magnesium sulfate. The solvent is then distilled off to obtain an oily substance. This oily substance is separated and purified by chromatography on silica gel. By the above procedure is obtained 184 mg of t-butyl 7β-phenylacetamido-7α-methoxydesacetoxycephalosporanate as crystals.

EXAMPLE 6

Benzyl 6β-phenylacetamido-6α-methoxypenicillanate

In tetrahydrofuran (10 ml) is dissolved benzyl 6β-di(β,β,β-trichloroethyl)phosphoramido-6α-methoxypenicillanate (679 mg) and the solution is stirred under cooling at −78° C. and under nitrogen streams. To this solution is added triethylamine (100 mg) together with n-butyl lithium (0.5 ml of 9% solution in n-hexane), and the reaction is carried out for 15 minutes. Then, following the addition of phenylacetyl chloride (154 mg), the reaction is further carried out at −78° C. for 30 minutes. Then, to the resultant acetic acid (0.5 ml) is added and, after a reaction time of 5 minutes the mixture is poured in water and extracted with ethyl acetate. The organic layer is taken, washed with a saturated aqueous solution of sodium bicarbonate and water, and dried over magnesium sulfate. The solvent is then distilled off, and the resultant oily substance is purified by chromatography on silica gel. By the above procedure is obtained 184 mg of benzyl 6β-phenylacetamido-6α-methoxypenicillanate as a powder.

EXAMPLE 7

Benzhydryl 7β-[2-(β,β,β-trichloroethoxycarbonylamino)thiazol-4-ylacetamido)-7α-methoxycephalosporanate In tetrahydrofuran (5 ml) is dissolved benzhydryl 7β-di-(β,β,β-trichloroethyl)phosphoramido-7α-methoxycephalosporanate (388 mg) and the solution is stirred under cooling at −78° C. and under nitrogen streams. To the solution is added triethylamine (100 mg) together with n-butyl lithium (0.5 ml of 9% solution in n-hexane) and the reaction is carried out for 15 minutes.

Then, to the mixture 2-(β,β,β-trichloroethoxycarbonylamino)thiazol-4-ylacetyl chloride (352 mg) is added and the reaction is further conducted for 30 minutes. Following the addition of acetic acid (0.5 ml), the reaction is carried out for 5 minutes. The reaction mixture is poured in a saturated aqueous solution of sodium bicarbonate and extracted with ethyl acetate. The organic layer is taken, washed with water and dried over magnesium sulfate. The solvent is then distilled off and the resultant oily substance is purified by chromatography on silica gel. By the above procedure is obtained benzhydryl 7β-[2-(β,β,β-trichloroethoxycarbonylamino)-thiazol-4-ylacetamido]-7α-methoxycephalosporanate as a powder.

REFERENCE EXPERIMENT

Sodium 7α-methoxy-7β-(2-aminothiazol-4-ylacetamido)-3-(1-methyl-1H-tetrazol-5-ylthiomethyl)-3-cephem-4-carboxylate (1) In 25 ml of 90% formic acid is dissolved 990 mg. of benzhydryl 7α-methoxy-7β[2-(β,β,β-trichloroethoxycarbonylamino)thiazol-4-ylacetamido]cephalosporanate and, after the addition of 860 mg zinc dust under cooling with ice, the mixture is stirred for 1 hour. The reaction mixture is poured in a saturated aqueous solution of sodium chloride and extracted with ethyl acetate. The ethyl acetate layer is washed with water, a 5% aqueous sodium hydrogen carbonate solution and a saturated aqueous sodium chloride solution in the order mentioned, followed by drying over magnesium sulfate. Thereafter, the ethyl acetate is distilled off to obtain 472 mg of benzhydryl 7α-methoxy-7β-(2-aminothiazol-4-ylacetamido)cephalosporanate. The infrared absorption spectrum of this product shows an absorption of β-lactam at 1770 cm$^{-1}$.

NMR(CDCl$_3$, δ): 2.00(s,3H,COCH$_3$), 3.36(q,2H,2-CH$_2$), 3.45(s, 3H,7-OCH$_3$), 3.56(s,2H,thiazolyl-CH$_2$CO),

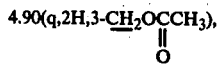
4.90(q,2H,3-CH$_2$OCCH$_3$),
              ‖
              O 5.08(s,1H,6-H), 6.28(s,1H,thiazole 5-H), 6.93(s,1H,-CH(C$_6$H$_5$)$_2$).

(2) Under cooling with ice and stirring, 335 mg of benzhydryl 7α-methoxy-7β-(2-aminothiazol-4-ylacetamido)cephalosporanate is added to a mixture of 1.5 ml trifluoroacetic acid and 1.5 ml anisole and the mixture is stirred for 30 minutes. The reaction mixture is poured in 50 ml anhydrous ether and the resultant white precipitate is collected and rinsed with ether. The procedure provides crude 7α-methoxy-7β-(2-aminothiazol-4-ylacetamido)cephalosporanic acid trifluoroacetate. This product is dissolved in a 5% aqueous solution of sodium hydrogen carbonate and the solution is run onto a column of Amberlite XAD-2(trade name) and eluted with water. This purification procedure provides 131 mg of sodium 7α-methoxy-7β-(2-aminothiazol-4-ylacetamido)cephalosporanate.trihydrate.

Elemental analysis, for C$_{16}$H$_{17}$O$_7$N$_4$S$_2$Na.3H$_2$O: Calcd.: C, 37.06; H, 4.47; N, 10.80. Found: C, 37.36; H, 4.14; N, 10.50.

NMR(D$_2$O, δ): 2.26(s,3H,3-COCH$_3$), 3.52(q,2H,2-CH$_2$), 3.70(s,3H,7-OCH$_3$), 3.80(s,2H,thiazolyl-CH$_2$CO),

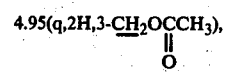
4.95(q,2H,3-CH$_2$OCCH$_3$),
              ‖
              O 5.32(s,1H,6-H), 6.70(s,1H,thiazole 5-H).

(3) In 4 ml of water containing 208 mg of sodium hydrogen carbonate, there are dissolved 431 mg of 7α-methoxy-7β-(2-aminothiazol-4-ylacetamido)cephalosporanic acid.trifluoroacetate, 108 mg of 1-methyl-1H-tetrazole-5-thiol and 24.6 mg of triethylbenzylammonium bromide, and the reaction mixture is stirred at 60° C. for 6 hours in an atmosphere of nitrogen gas. After cooling, the reaction mixture is passed through a column of Amberlite XAD-2(trade name) and eluted with water. The above purification procedure provides 158 mg of sodium 7α-methoxy-7β-(2-aminothiazol-4-ylacetamido)3-(1-methyl-1H-tetrazol-5-ylthiomethyl)-3-cephem-4-carboxylate.

Elemental analysis, for C$_{16}$H$_{17}$O$_5$N$_8$SNa.H$_2$O: Calcd.: C, 35.68; H, 3.55; N, 20.86. Found: C, 35.56; H, 3.36; N, 19.83.

The infrared absorption spectrum (KBr) of this product shows an absorption of β-lactam at 1750 cm$^{-1}$.

NMR(D$_2$O, δ): 3.60(q,2H,2-CH$_2$), 3.65(s,3H,7-OCH$_3$), 3.77(s, 2H,thiazolyl-CH$_2$CO), 4.17(s,3H,N-CH$_3$), 4.30(q,2H, 3-CH$_2$), 5.24(s,1H,6-H), 6.67(s,1H,thiazole 5-H).

The antibiotic activity of sodium 7α-methoxy-7β-(2-aminothiazol-4-ylacetamido)-3-(1-methyl-1H-tetrazol-5-ylthiomethyl)-3-cephem-4-carboxylate obtained in the reference experiment is shown as follows.

| Microorganism | MIC(γ/ml) |
|---|---|
| S. aureus 209p | 1.56 |
| S. aureus 1840 | 3.13 |
| S. aureus Fs 40204 | 3.13 |
| E. coli NIHJ | 1.56 |
| E. coli 0-111 | 0.78 |
| E. coli T-7 | 6.25 |
| K. pneumoniae DT | 0.78 |
| K. pneumoniae GN 3835 | 1.56 |
| Ps. aeruginosae PM3 | 6.25 |
| Serr. marcescens IFO 12648 | 6.25 |
| Serratia TN0024 | 6.25 |
| P. vulgaris GN 4413 | 6.25 |

What we claim is:
1. A compound of the formula

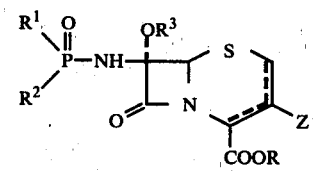

wherein
R$^1$ and R$^2$, independently of each other, are alkoxy of 1-4 carbon atoms, alkoxy of 1-4 carbon atoms substituted by halogen, benzyloxy, phenyl, phenoxy, or phenoxy substituted by one member selected from the group consisting of nitro, methyl, methoxy and halogen, R$^3$ is methyl, R is selected from the group consisting of hydrogen, benzyl, p-nitrobenzyl, p-halogenobenzyl, pivaloyloxymethyl, dimethylsilyl, trimethylsilyl, methoxysilyl, benzhydryl, methoxymethyl, trichloroethyl, methylsulfonylethyl, benzoylmethyl, t-butyl, methoxybenzyl, trityl, methylthiomethyl, α-acetoxybutyl and 1-pivaloyloxy-ethane-1-yl, and Z is a group of the formula —CH$_2$X where X is selected from the group consisting of (1) hydrogen, (2) alkoxy of 1–3 carbon atoms, (3) alkylthio of 1–3 carbon atoms, (4) azido, (5) carbamoyloxy, (6) carbamoyloxy substituted by alkyl of 1–3 carbon atoms, (7) thiocarbamoylthio, (8) aliphatic acyloxy selected from the group consisting of acetyloxy, propionyloxy and butyryloxy, and (9) heterocyclylthio selected from the group consisting of pyridylthio, N-oxide-pyridylthio, pyrimidylthio, pyridazinylthio, N-oxide-pyridazinylthio, pyrazolylthio, diazolylthio, thiazolylthio, 1,2,3-thiazolylthio, 1,2,4-thiadiazolylthio, 1,3,4-thiadiazolylthio, 1,2,5-thiadiazolylthio, 1,2,3-oxadiazolylthio, 1,2,4-oxadiazolylthio, 1,3,4-oxadiazolylthio, 1,2,5-oxadiazolylthio, 1,2,3-triazolylthio, 1,2,4-triazolylthio, 1H-tetrazolylthio and 2H-tetrazolylthio, each of said heterocyclylthio groups being unsubstituted or substituted by at least one member selected from the group consisting of alkyl of 1–3 carbon atoms, alkoxy of 1–3 carbon atoms, halogen, trifluoromethyl, trichloroethyl, hydroxyl, mercapto, amino, carboxyl and carbamoyl, the sulfur atom in the above formula (II) being in the oxide or non-oxide form, or a salt of said compound.

2. A compound as claimed in claim 1, wherein the compound is a 3-cephem compound.

3. A compound as claimed in claim 1, wherein the heterocyclylthio group is thiadiazolylthio, oxadiazolylthio, triazolylthio or tetrazolylthio.

4. A compound as claimed in claim 1, wherein X is a member selected from the group consisting of hydrogen, acetyloxy, azido, carbamoyloxy, methoxy, methylthio, thiocarbamoylthio, methylcarbamoyloxy, (5-methyl-1,3,4-thiadiazol-2-yl) thio, (1-methyl-1H-tetrazol-5-yl)thio, (1H-1,2,3-triazol-5-yl)thio, and (5-methyl-1,3,4-oxadiazol-2-yl)thio.

5. A compound as claimed in claim 1, wherein R is hydrogen or a member selected from the group consisting of t-butyl, benzyl, benzhydryl, methylsulfonylethyl, methoxymethyl, trimethylsilyl, p-nitrobenzyl and p-bromobenzyl.

6. A compound as claimed in claim 1, wherein the compound is t-butyl 7β-dimethylphosphoramido-7α-methoxydesacetoxycephalosporanate.

7. A compound as claimed in claim 1, wherein the compound is t-butyl 7β-diphenylphosphinylamino-7α-methoxydesacetoxycephalosporanate.

8. A compound as claimed in claim 1, wherein the compound is t-butyl 7β-diphenylphosphoramido-7α-methoxydesacetoxycephalosporanate.

9. A compound as claimed in claim 1, wherein the compound is t-butyl 7β-di(β,β,β-trichloroethyl)phosphoramido-7α-methoxydesacetoxycephalosporanate.

10. A compound as claimed in claim 1, wherein the compound is benzhydryl 7β-di(β,β,β-trichloroethyl)-phosphoramido-7α-methoxycephalosporanate.

11. A compound as claimed in claim 1, wherein R$^1$ and R$^2$, independently of each other, are selected from the group consisting of methoxy, ethoxy, propoxy, butoxy, β,β,β-trichloroethoxy, phenyl, phenoxy, p-nitrophenoxy, p-methylphenoxy, benzyloxy, p-methoxyphenoxy and m-chlorophenoxy.

12. A compound as claimed in claim 1, wherein the salt is a sodium, potassium, lithium, triethylammonium or tributylammonium salt.

* * * * *